United States Patent [19]

Nelson

[11] 4,238,508

[45] Dec. 9, 1980

[54] METHOD FOR ANALGESIA USING 3-HYDROXYACETANILIDE

[75] Inventor: Edward B. Nelson, Williamsville, N.Y.

[73] Assignee: The Research Foundation of State University of New York, Albany, N.Y.

[21] Appl. No.: 67,348

[22] Filed: Aug. 17, 1979

[51] Int. Cl.³ .................................... A61K 31/165
[52] U.S. Cl. ............................................ 424/324
[58] Field of Search ...................................... 424/324

[56] References Cited

FOREIGN PATENT DOCUMENTS 1006558 10/1965 United Kingdom .

Primary Examiner—Stanley J. Friedman

[57] ABSTRACT

A method for providing analgesia to warm blooded animals which comprises administering sufficient 3-hydroxyacetanilide of the formula:

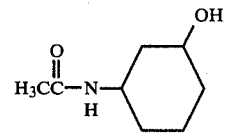

9 Claims, No Drawings

METHOD FOR ANALGESIA USING 3-HYDROXYACETANILIDE

The invention described herein was made in the course of work under a grant or award from the Department of Health, Education and Welfare.

BACKGROUND OF THE INVENTION (a) Field of the Invention

This invention relates to analgesic pharmaceutical compositions (i.e., compositions for reducing pain) in warm blooded animals. In particular, the invention relates to acetanilide related analgesic compositions.

(b) History of the Prior Art

Historically, there has been a search for methods of reducing pain in warm blooded animals and especially in human beings. The search for a safe, effective analgesic composition, which can be administered to warm blooded animals, has therefore been a continuing one since better safety and effectiveness are always desirable.

One of the most common analgesic compositions for reducing pain is aspirin or sodium acetylsalicylate. Unfortunately, aspirin has some undesirable effects especially in some individuals who are sensitive to aspirin. This sensitivity can take the form of upset stomachs and G.I. disturbances and can be allergic reactions which in uncommon cases can even cause death.

For these reasons, acetaminophen, also known as 4-hydroxyacetanilide, was developed and is marketed as an analgesic for use by those who are sensitive to aspirin. Unfortunately, while acetaminophen seems to cause fewer gastro intestinal disturbances, at least some allergic reactions do occur. Furthermore, the toxicity of acetaminophen is undesirably high and liver damage and even death can result from ingestion of excessive quantities of acetaminophen.

It has been previously known, for example as disclosed in British Pat. No. 1,006,558 that 3-hydroxyacetanilide (m-hydroxyacetanilide, 3OH acetanilide) has anti-pyretic activity, (i.e., can reduce fevers). It has not, however, been previously known that 3-hydroxyacetanilide has analgesic properties. 3-hydroxyacetanilide is known to be substantially less hepatotoxic than acetaminophen (see Acetaminophen Structure Toxicity Relationships: Why is 3-hydroxyacetanilide Not Hepatotoxic? *Stanley A. Roberts* and *David J. Jollow*. Medical University of South Carolina, Charlston, S.C.)

BRIEF DESCRIPTION OF THE INVENTION

In accordance with the invention, there is provided a method for providing analgesia to warm blooded animals including mammals such as mice, cats, dogs and humans, which comprises administering sufficient 3-hydroxyacetanilide having the formula:

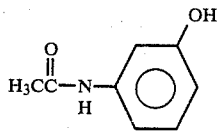

The quantity of 3-hydroxyacetanilide sufficient to cause analgesia is dependent upon the size of the warm blooded animal involved and somewhat dependent upon the species of animal involved. In general, for most applications, from about 2 to about 400 milligrams per kilogram of body weight of 3-hydroxyacetanilide is used in accordance with the method of the invention. In general, larger animals require less of any pharmaceutical compound per kilogram of body weight than smaller animals. For humans and other animals, 3-hydroxyacetanilide should be used at dosages similar to the known dosages of aspirin and acetaminophen, e.g., about 3 to about 12 milligrams per kilogram of body weight for humans for a total of 300 to 900 milligrams per dose.

The 3-hydroxyacetanilide can be administered orally, subcutaneously, intraperitoneally, intravenously or rectally. The preferred method of administration when tests are not being conducted is orally.

The 3-hydroxyacetanilide can be administered to cause analgesia either alone or in conjunction with inert pharmaceutical carriers or diluents or in conjunction with at least one other pharmaceutically active compound. Examples of inert diluents are water, talc, starch, gum acacia, magnesium stearate, lactose, sucrose, calcium phosphate, vegetable or mineral oils or waxes, and methyl cellulose. Examples of active ingredients which may be used in conjunction with the 3-hydroxyacetanilide are acetylsalicylic acid or sodium acetylsalicylate, aluminum aspirin, aspirin anhydride, caffeine and codeine phosphate. Essentially any inert ingredient or active ingredient can be administered in combination with the 3-hydroxyacetanilide provided adverse in vivo reactions or adverse chemical reactions do not occur as a result of the combination.

DETAILED DESCRIPTION OF THE INVENTION

The following examples serve to illustrate and not limit the analgesic method of the invention and to illustrate the relatively low toxicity of 3-hydroxyacetanilide.

EXAMPLE 1

Example 1 illustrates the relatively low toxicity of 3-hydroxyacetanilide as compared with acetaminophen. Doses of 400, 600 and 900 milligrams per kilogram of 3-hydroxyacetanilide, of acetaminophen and of normal saline control were administered to white mice. As illustrated in Table 1, 3-hydroxyacetanilide caused considerably less mortality than a comparable dose of acetaminophen and in addition, the livers from the mice which died from an injection of acetaminophen were large and grossly congested in appearance; whereas, no significant gross abnormality of the liver was obvious from deaths caused by 3-hydroxyacetanilide.

At the high dose of 3-hydroxyacetanilide (900 mg/kg), the animals became sedated after injection of the drug. The loss of righting reflex behavior was noted to last several hours. Unless death ensued, they regained usual behavior by the next day.

TABLE I

Mortality in Mice - Comparison of 3-Hydroxyacetanilide to Acetaminophen

| Drug Treatment | Dose | No. | Survivors | % Survivors |
|---|---|---|---|---|
| Saline | — | 33 | 33 | 100%[b] |
| 3OH Acetanilide | 400 mg/kg | 41 | 40 | 96%[b] |
| 3OH Acetanilide | 600 mg/kg | 25 | 24 | 96%[b] |
| 3OH Acetanilide | 900 mg/kg | 24 | 22 | 91%[b] |
| Acetaminophen | 400 mg/kg | 41 | 18 | 40% |
| Acetaminophen | 600 mg/kg | 25 | 5 | 20% |

TABLE I-continued
Mortality in Mice - Comparison of 3-Hydroxyacetanilide to Acetaminophen

| Drug Treatment | Dose | No. | Survivors | % Survivors |
|---|---|---|---|---|
| Acetaminophen | 900 mg/kg | 25 | 5 | 20% |

(a)Mortality determined at 96 hours, all drugs given intraperitoneally dissolved in saline at 42° C.
(b)Survival significantly different from acetaminophen group receiving same mg dose or saline controls and all acetaminophen groups p <0.005 using chi square test.

EXAMPLE 2

A number of mice were given doses of acetaminophen and 3-hydroxyacetanilide at levels of 600 mg/kg of body weight and a number of mice were given normal saline as a control. Large doses of acetaminophen were shown to lead to rapid depletion of mouse liver glutathione levels in the liver with much less depletion caused by 3-hydroxyacetanilide. The results are set forth in Table II. All values were determined at two hours after intraperitoneal drug injection.

TABLE II
Effect of 3-Hydroxyacetanilide and Acetaminophen on Liver Glutathione Levels

| Drug Treatment | Dose | n | Level (mg/gram liver) |
|---|---|---|---|
| Saline | — | 10 | 8.2 ± 0.9 |
| 3OH Acetanilide | 600 mg/kg | 10 | 6.2 ± 1.2 |
| Acetaminophen | 600 mg/kg | 8 | 2.4 ± 0.6 |

EXAMPLE 3

The relative effects of 3-hydroxyacetanilide and acetaminophen were compared on plasma glutamate-pyruvate transaminase (GPT) activity. 600 mg/kg of acetaminophen were used in the test; whereas, a larger quantity, 900 mg/kg, of 3-hydroxyacetanilide was used. Even at the smaller dose, it is apparent that acetaminophen drastically affects the transaminase activity; whereas, the much larger dose of 3-hydroxyacetanilide has much less effect. Activity was measured spectrophotometrically at room temperature using a Sigma ® Enzyme Kit. The activity is expressed in micromoles per minute per millimeter of plasma. The blood for the test was collected in a small amount of heparin. Assays were performed within two hours after obtaining the blood. The results of the test are shown in Table III. Acetaminophen-induced hepatic injury results in centrilobular necrosis with simultaneous elevation in plasma transaminase levels to maximum levels at approximately 6 hours after the dose in mice. There appears to be a correlation between drug dose, amounts of necrosis seen histologically and elevation of transaminase levels. It was found that 3-hydroxyacetanilide did not cause a similar level of hepatic necrosis nor did it drastically affect plasma GPT. No significant elevation in plasma GPT activity has been observed up to 48 hours after treatment with 900 mg/kg of 3-hydroxyacetanilide.

TABLE III
Effect of 3-Hydroxyacetanilide and Acetaminophen on Plasma Glutamate-Pyruvate Transaminase Levels in Mice

| Drug | Dose | n | Transaminase Activity IU/ml Plasma Mean ± SD |
|---|---|---|---|
| Saline | — | 32 | 32 ± 18 |
| Acetaminophen | 600 mg/kg | 9 | 1834 ± 771 |
| 3-Hydroxyacetanilide | 900 mg/kg | 17 | 23 ± 5 |

EXAMPLE 4

To test the effectiveness of 3-hydroxyacetanilide as an analgesic when compared to acetaminophen, a mouse writhing test was used wherein 1% acetic acid is given intraperitoneally 5 minutes prior to counting abdominal writhes made by the animal. The dose of the 1% actic acid given is 0.01 cc/gm of body weight. Prior to counting the writhes, acetaminophen and 3-hydroxyacetanilide were given subcutaneously 30 minutes prior to the test. The control was given normal saline. The results are shown in Table IV. Table IV clearly illustrates that while the average number of writhes per 5 minutes with the control was 23.2, both 3-hydroxyacetanilide and acetaminophen effectively reduced the number of writhes per 5 minutes with statistically insignificant differences. This example therefore illustrates that 3-hydroxyacetanilide is unexpectedly as good an analgesic in this test as acetaminophen and should therefore be used in dosages similar to the dosages known to be effective for actaminophen and since it has almost the same analgesic effect in mice as acetaminophen, it would be expected to have the same analgesic effect as acetaminophen in other mammals.

TABLE IV
Effectiveness of 3-Hydroxyacetanilide as an Analgesic Compared to Acetaminophen Mouse Writhing Test with 1% Acetic Acid

| Treatment | n | Writhes per 5 Minute(SD) |
|---|---|---|
| Control | 37 | 23.2 ± 5.3 |
| 3OH Acetanilide | | |
| 200 mg/kg | 10 | 11.6 ± 8.1 |
| 400 mg/kg | 11 | 1.3 ± 1.4 |
| Acetaminophen | | |
| 200 mg/kg | 10 | 10.0 ± 6.2 |
| 400 mg/kg | 10 | 3.5 ± 4.0 |

What is claimed is:

1. A method for providing analgesia which comprises administering to a warm blooded animal in need of analgesia, sufficient 3-hydroxyacetanilide in a quantity of from about 3 to about 400 milligrams per kilogram of body weight of the animal said 3-hydroxyacetanilide being of the formula:

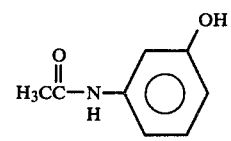

2. The method of claim 1 wherein the warm blooded animal is a mammal.
3. The method of claim 2 wherein the sufficient 3-hydroxyacetanilide is from about 3 to about 12 milligrams per kilogram of body weight.
4. The method of claim 2 wherein the 3-hydroxyacetanilide is administered orally.
5. The method of claim 2 wherein the 3-hydroxyacetanilide is administered subcutaneously.
6. The method of claim 2 wherein the 3-hydroxyacetanilide is compounded with at least one inert pharmaceutical carrier or diluent.
7. The method of claim 2 wherein the 3-hydroxyacetanilide is orally administered in tablet form.
8. The method of claim 2 wherein the 3-hydroxyacetanilide is administered intraperitoneally.
9. The method of claim 4 wherein the dosage is about 3 to about 12 milligrams per kilogram of body weight.

* * * * *